(12) United States Patent
Bastian et al.

(10) Patent No.: US 7,704,253 B2
(45) Date of Patent: Apr. 27, 2010

(54) SINGLE USE RESECTION GUIDE

(75) Inventors: Adam Bastian, Chester, NY (US); Scott Harrington, Westwood, NJ (US); Mark Nemec, Goshen, NY (US); Philip F. Williams, III, Teaneck, NJ (US); Alex F. Canonaco, Caldwell, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 573 days.

(21) Appl. No.: 11/368,562

(22) Filed: Mar. 6, 2006

(65) Prior Publication Data
US 2007/0208349 A1 Sep. 6, 2007

(51) Int. Cl.
*A61B 17/00* (2006.01)

(52) U.S. Cl. ............... 606/82; 606/79; 606/87; 606/88

(58) Field of Classification Search .......... 606/82, 606/87, 88, 178
See application file for complete search history.

(56) References Cited

U.S. PATENT DOCUMENTS

| | | |
|---|---|---|
| 3,229,006 A | 1/1966 | Nohl |
| 3,624,747 A | 11/1971 | McKnight |
| 3,807,393 A | 4/1974 | McDonald |
| 3,911,923 A | 10/1975 | Yoon |
| 3,920,022 A | 11/1975 | Pastor |
| 3,967,625 A | 7/1976 | Yoon |
| 3,989,049 A | 11/1976 | Yoon |
| 3,991,426 A | 11/1976 | Flom et al. |
| 3,994,287 A | 11/1976 | Turp et al. |
| 4,053,953 A | 10/1977 | Flom et al. |
| 4,085,743 A | 4/1978 | Yoon |
| 4,103,680 A | 8/1978 | Yoon |
| 4,299,224 A | 11/1981 | Noiles |
| 4,311,145 A | 1/1982 | Esty et al. |
| 4,374,523 A | 2/1983 | Yoon |
| 4,421,112 A | 12/1983 | Mains et al. |
| 4,509,518 A | 4/1985 | McGarry et al. |
| 4,545,375 A | 10/1985 | Cline |
| 4,619,391 A | 10/1986 | Sharkany et al. |
| 4,624,254 A | 11/1986 | McGarry et al. |
| 4,641,648 A | 2/1987 | Shapiro |
| 4,662,372 A | 5/1987 | Sharkany et al. |
| 4,682,598 A | 7/1987 | Beraha |
| 4,685,460 A | 8/1987 | Thornton |
| 4,721,104 A | 1/1988 | Kaufman et al. |
| 4,817,602 A | 4/1989 | Beraha |

(Continued)

FOREIGN PATENT DOCUMENTS

EP    1 559 375    8/2005

(Continued)

*Primary Examiner*—Eduardo C Robert
*Assistant Examiner*—Julianna N Harvey
(74) *Attorney, Agent, or Firm*—Lerner, David, Littenberg, Krumholz & Mentlik, LLP

(57) ABSTRACT

Single use or disposable cutting blocks and methods for utilizing same are disclosed. The blocks are preferably constructed of polymer and/or other suitable low cost and light weight materials. The blocks may be adapted for use with low friction cutting instruments, as well as other such cutting instruments. Several differently sized and configured blocks may be utilized to perform a single surgical procedure. In addition, kits housing one or more such blocks, with or without other instruments are possible.

22 Claims, 16 Drawing Sheets

U.S. PATENT DOCUMENTS

| | | | | |
|---|---|---|---|---|
| 4,926,847 | A | * | 5/1990 | Luckman .................... 606/88 |
| 4,961,954 | A | | 10/1990 | Goldberg et al. |
| 4,985,038 | A | | 1/1991 | Lyell |
| 5,060,678 | A | | 10/1991 | Bauman et al. |
| 5,098,437 | A | | 3/1992 | Kashuba et al. |
| 5,100,689 | A | | 3/1992 | Goldberg et al. |
| 5,111,987 | A | | 5/1992 | Moeinzadeh et al. |
| 5,123,906 | A | | 6/1992 | Kelman |
| 5,152,744 | A | | 10/1992 | Krause et al. |
| 5,152,778 | A | | 10/1992 | Bales, Jr. et al. |
| 5,170,800 | A | | 12/1992 | Smith et al. |
| 5,171,243 | A | | 12/1992 | Kashuba et al. |
| 5,174,300 | A | | 12/1992 | Bales et al. |
| 5,176,702 | A | | 1/1993 | Bales et al. |
| 5,178,622 | A | | 1/1993 | Lehner, II |
| 5,183,053 | A | | 2/1993 | Yeh et al. |
| 5,186,178 | A | | 2/1993 | Yeh et al. |
| 5,197,968 | A | | 3/1993 | Clement |
| 5,207,692 | A | | 5/1993 | Kraus et al. |
| 5,258,004 | A | | 11/1993 | Bales et al. |
| 5,273,524 | A | | 12/1993 | Fox et al. |
| 5,275,166 | A | | 1/1994 | Vaitekunas et al. |
| 5,293,878 | A | | 3/1994 | Bales et al. |
| 5,322,505 | A | | 6/1994 | Krause et al. |
| 5,348,541 | A | | 9/1994 | Lyell |
| 5,368,599 | A | | 11/1994 | Hirsch et al. |
| 5,425,745 | A | | 6/1995 | Green et al. |
| 5,454,815 | A | | 10/1995 | Geisser et al. |
| 5,454,816 | A | | 10/1995 | Ashby |
| 5,456,720 | A | | 10/1995 | Schultz et al. |
| 5,472,415 | A | | 12/1995 | King et al. |
| 5,484,095 | A | | 1/1996 | Green et al. |
| 5,490,854 | A | | 2/1996 | Fisher et al. |
| 5,497,933 | A | | 3/1996 | DeFonzo et al. |
| 5,522,897 | A | | 6/1996 | King et al. |
| 5,540,696 | A | | 7/1996 | Booth, Jr. et al. |
| 5,554,169 | A | | 9/1996 | Green et al. |
| 5,569,163 | A | | 10/1996 | Francis et al. |
| 5,570,700 | A | | 11/1996 | Vogeler |
| 5,649,946 | A | | 7/1997 | Bramlet |
| 5,667,069 | A | | 9/1997 | Williams, Jr. |
| 5,690,635 | A | | 11/1997 | Matsen, III et al. |
| 5,702,460 | A | | 12/1997 | Carls et al. |
| 5,707,350 | A | | 1/1998 | Krause et al. |
| 5,712,543 | A | | 1/1998 | Sjostrom |
| 5,716,361 | A | * | 2/1998 | Masini .................... 606/86 R |
| 5,718,708 | A | | 2/1998 | Webb |
| 5,755,731 | A | | 5/1998 | Grinberg |
| 5,792,139 | A | | 8/1998 | Chambers et al. |
| 5,817,097 | A | | 10/1998 | Howard et al. |
| 5,817,109 | A | | 10/1998 | McGarry et al. |
| 5,871,493 | A | | 2/1999 | Sjostrom et al. |
| 5,899,914 | A | | 5/1999 | Zirps et al. |
| 5,913,874 | A | | 6/1999 | Berns et al. |
| 5,921,990 | A | | 7/1999 | Webb |
| 5,997,566 | A | | 12/1999 | Tobin |
| 6,015,419 | A | | 1/2000 | Strome et al. |
| 6,077,287 | A | | 6/2000 | Taylor et al. |
| 6,090,122 | A | | 7/2000 | Sjostrom et al. |
| 6,099,532 | A | | 8/2000 | Florea |
| 6,174,321 | B1 | | 1/2001 | Webb |
| 6,258,095 | B1 | | 7/2001 | Lombardo et al. |
| 6,325,806 | B1 | | 12/2001 | Fox |
| 6,328,572 | B1 | | 12/2001 | Higashida et al. |
| 6,338,737 | B1 | | 1/2002 | Toledano |
| 6,391,040 | B1 | | 5/2002 | Christoudias |
| 6,409,722 | B1 | | 6/2002 | Hoey et al. |
| 6,431,743 | B1 | | 8/2002 | Mizutani et al. |
| 6,500,181 | B1 | | 12/2002 | Portney |
| 6,514,259 | B2 | | 2/2003 | Picard et al. |
| 6,558,391 | B2 | | 5/2003 | Axelson, Jr. et al. |
| 6,589,283 | B1 | | 7/2003 | Metzger et al. |
| 2003/0028196 | A1 | | 2/2003 | Bonutti |
| 2003/0171757 | A1 | | 9/2003 | Coon et al. |
| 2004/0015173 | A1 | | 1/2004 | Irving |
| 2004/0243134 | A1 | | 12/2004 | Walker et al. |
| 2005/0171545 | A1 | | 8/2005 | Walsh et al. |
| 2005/0192584 | A1 | | 9/2005 | Walker et al. |
| 2005/0228393 | A1 | * | 10/2005 | Williams et al. .............. 606/87 |
| 2005/0234461 | A1 | | 10/2005 | Burdulis et al. |
| 2005/0240196 | A1 | | 10/2005 | Davis et al. |
| 2005/0267485 | A1 | | 12/2005 | Cordes et al. |
| 2006/0009796 | A1 | * | 1/2006 | Carusillo et al. ............ 606/178 |
| 2007/0119055 | A1 | | 5/2007 | Walen et al. |

FOREIGN PATENT DOCUMENTS

| | | | |
|---|---|---|---|
| EP | 1 559 375 A1 | * | 8/2005 |
| WO | 97/29697 | | 8/1997 |
| WO | 2005/084558 | | 9/2005 |

* cited by examiner

SINGLE USE RESECTION GUIDE

BACKGROUND OF THE INVENTION

The present invention relates to the field of orthopedic surgery, and in particular, to disposable resection guides and methods of utilizing same for use during total joint replacement surgery.

Many surgical operations call for the accurate and precise cuts of bone or bone material. Typically, these cuts, or resections, are made using surgical saws or milling devices. These instruments, while excellent at actually performing such cuts, often times require the use of external guides in surgical procedures calling for accurate cuts. For example, a surgeon performing a total knee arthroplasty must make several cuts in the distal end of the femur to properly fit a prosthetic femoral component thereon. The position of such cuts ultimately determines the positioning and stability of the femoral component. Thus, if such resections are incorrectly made, the surgery can result in failure and require further corrective procedures.

For this and other reasons, surgeons often employ the use of surgical cutting guides, known also as cutting blocks. These blocks typically include guiding surfaces which aid in guiding the cutting device during the cutting of the bone material. These guiding surfaces may simply be flat surfaces, or in certain cases, open slots which allow a cutting instrument to be inserted and guided therethrough. One specific type of cutting block is a block utilized during a total knee arthroplasty having four guiding surfaces utilized to create four cuts on an already at least partially resected distal portion of the femur. These guides are typically mounted on a prepared distal femoral surface, and the four cuts are generally referred to as anterior and posterior cuts, and anterior and posterior chamfer cuts. Examples of these femoral cutting blocks are shown in U.S. Pat. No. 5,454,816 to Ashby, U.S. Pat. No. 6,258,095 to Lombardo et al., U.S. Pat. No. 6,558,391 to Axelson, Jr. et al, and U.S. Pat. App. Pub. No. 2005/0228393 to Williams et al., the respective disclosures of which are hereby incorporated by reference herein.

While cutting blocks such as those described above are useful in performing the various cuts on a bone, they have their drawbacks. Most importantly, the manufacturing costs associated with such blocks are often quite high. A standard block is typically constructed of a suitable metallic material machined from a solid block or from several solid pieces of a suitable metallic material assembled together to provide a block with one or more guiding surfaces which allow for the various cuts to be accurately and precisely performed. These materials and the manufacture and manipulation of same are generally costly. Often times, these relatively high manufacturing costs, require the expensive cutting blocks to be utilized in multiple surgeries. This re-use often requires the cleaning and sterilization of such a block prior to each use, which necessarily adds an additional per-use cost.

Further to the high manufacturing and per-use costs of utilizing such well known cutting blocks, multiple uses of a single block may cause the guiding surfaces or the like of such blocks to become less accurate and precise. More particularly, multiple uses of such devices may allow for the greater chance of misaligning a cutting tool, such as a flat oscillating saw blade, due to wear of the cutting guide surfaces. In addition, even the most widely utilized sterilization procedures may not totally prevent the spread of dangerous bacteria or the like, which may in turn cause life threatening infections or other illnesses. Hence, a cheap, single use cutting block would be advantageous for use in common orthopedic procedures.

Therefore, there exists a need for a single use cutting block that can be inexpensively manufactured, while maintaining the required precise and accurate guiding surfaces needed for making cuts.

SUMMARY OF THE INVENTION

A first aspect of the present invention is a method of performing a surgical procedure on a patient. In accordance with a first embodiment of this first aspect, the method may include the steps of providing at least one cutting block constructed of polymeric material, the cutting block having at least one guiding surface, providing a low friction cutting instrument suitable for cutting a bone of the patient, the cutting instrument having an oscillating portion and a non-oscillating portion, positioning the cutting block with respect to the bone of the patient and cutting a portion of the bone of the patient by guiding the low friction cutting instrument along the guiding surface of the cutting block. According to a preferred method, the oscillating portion of the cutting instrument preferably cuts the bone of the patient and the non-oscillating portion of the cutting instrument is preferably guided by the guiding surface of the cutting block.

The surgical procedure of the first aspect may be a total knee arthroplasty. Three cutting blocks may be utilized including a first cutting block adapted to make a single resection across the distal end of a femur of the patient, a second cutting block adapted to make anterior and posterior resections of the femur of the patient and a third cutting block adapted to make anterior and posterior chamfer resections of the femur of the patient. Further, the first cutting block may be J-shaped. The method may also include the step of affixing the cutting block to the bone of the patient. In accordance with certain embodiments of the first aspect, the cutting block or blocks may include non-polymer elements. In addition, the cutting instrument may be a surgical saw including a blade assembly having an oscillating blade head, and may or may not further include a motor, a battery and a trigger. Finally, it is noted that the positioning step may include the use of a navigation tracker.

A second aspect of the present invention is a kit for use in performing a surgical procedure. In accordance with at least one embodiment of the second aspect, the kit may include at least one cutting block constructed of a polymeric material and at least one cutting instrument suitable for use of the cutting block. The cutting instrument in accordance with this embodiment may include an oscillating portion and a non-oscillating portion.

The kit may also include a plurality of bone connecting means selected from the group consisting of pins, screws and nails. In one embodiment, the kit may include three cutting blocks wherein a first cutting block is adapted to make a single resection across the distal end of a femur of the patient, a second cutting block is adapted to make a anterior and posterior resections of the femur of the patient and a third cutting block is adapted to make anterior and posterior chamfer resections of the femur of the patient. Further, the first cutting block may be J-shaped. Still further, the cutting instrument may be a blade assembly for use with a surgical saw, the blade assembly having an oscillating blade head, wherein the blade assembly is adapted for use with a handpiece having a motor, a battery and a trigger. In certain preferred embodiments, the kit may be sterilizably packaged. Additionally, the kit may include one or more navigation trackers. Finally, it is contemplated to utilize two or more kits to perform a single surgery. For example, one kit which is site specific and one kit which is non-site specific. A site specific kit may include, for instance, one or more blocks adapted for making specific cuts on specific bone and, possibly, one or more trial implants directed to the specific bone, while a non-site specific kit may include one or more blade assemblies and one or more universal blocks which may be utilized in making cuts on different bones.

DETAILED DESCRIPTION

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

The present invention relates to polymeric or otherwise relatively inexpensive cutting blocks or the like, as well as the use of such apparatus. These blocks may be designed for use in various surgical procedures. For example, as will be disclosed further below, blocks may be designed for use in a total knee arthroplasty. However, it is to be understood that blocks are contemplated for use in many different surgical procedures, such as surgeries relating to the shoulder joint, hip joint, spine, among other body portions. In addition, certain cutting blocks may be discussed herein in relation to use on a single bone or bone surface. However, such blocks may easily be modified, sized and/or configured for use in accordance with other portions of a patient's body.

Figure 1:
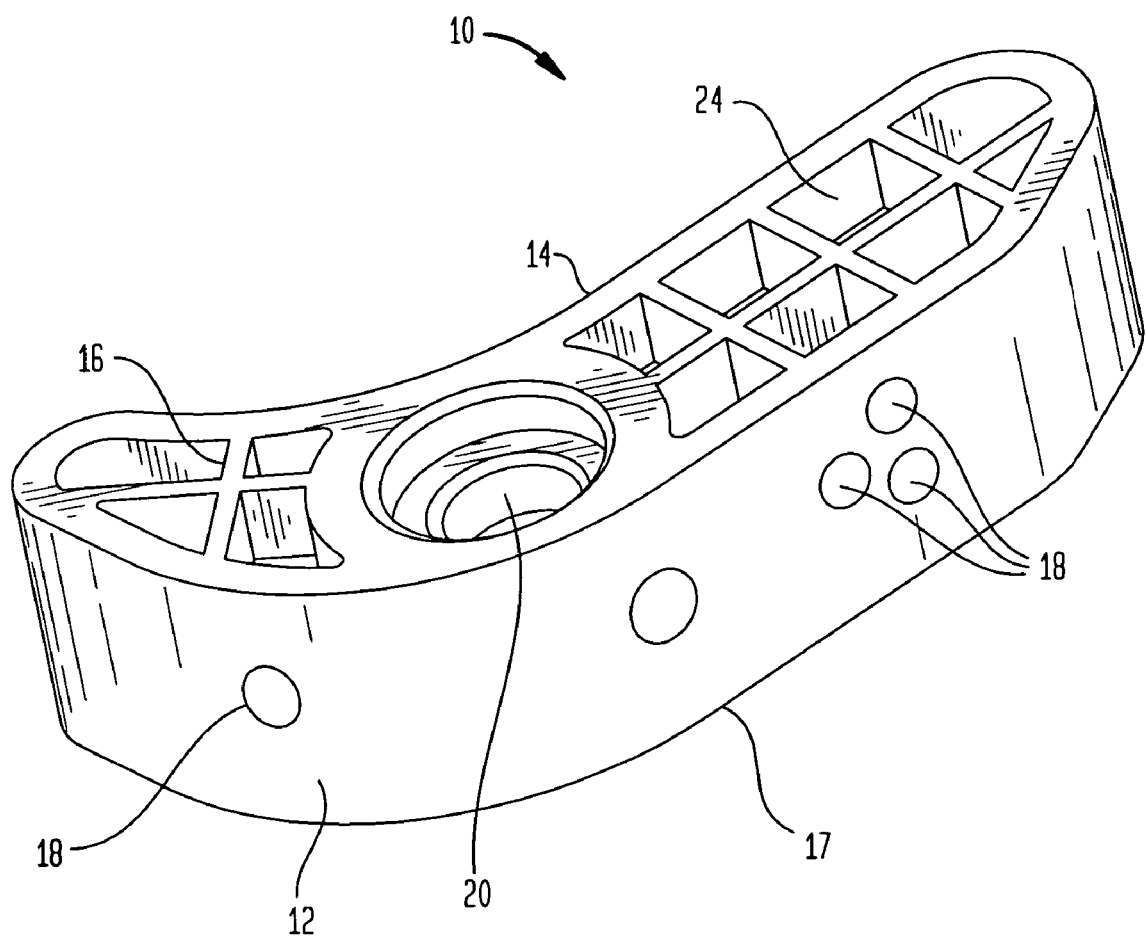
FIG. 1 is a perspective view of a J-block cutting guide apparatus according to the present invention.
Figure 2:
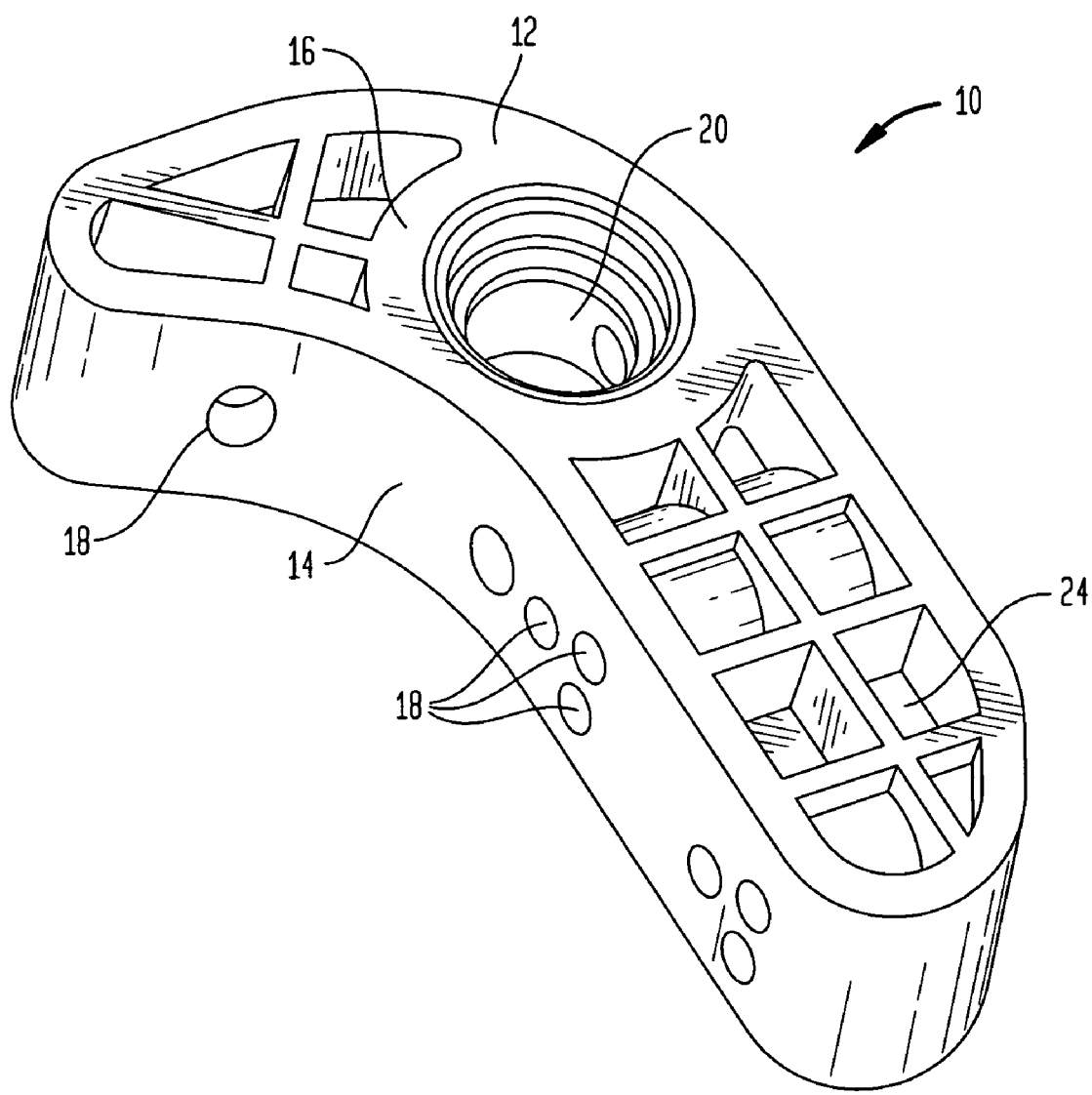
FIG. 2 is a perspective view of the bone contacting surface of the J-block shown in FIG. 1.
Figure 3:
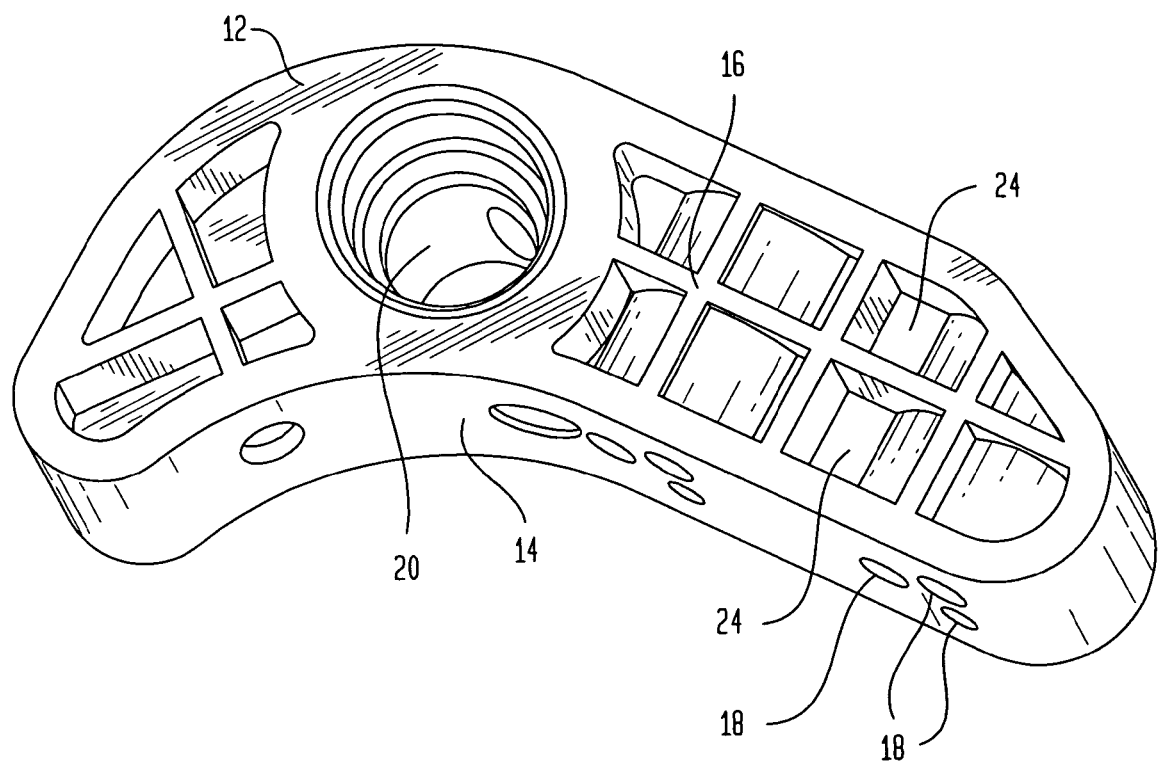
FIG. 3 is a perspective view of the distal facing surface of the J-block shown in FIG. 1.

Referring to the drawings, wherein like reference numerals represent like elements, there is shown in FIGS. 1-3 a cutting block suitable for aiding in performing a distal femoral resection during a total knee arthroplasty or similar surgery. Given its shape, this cutting block may be referred to a "J-block" and will be designated throughout by reference numeral 10. It is noted that a similar shaped cutting block is disclosed in commonly owned U.S. App. Pub. No. 2005/0171545 to Walsh et al., the disclosure of which is hereby incorporated by reference herein. However, in accordance with the present invention, J-block 10 is constructed mostly of a polymeric material or the like. For example, block 10 may be constructed of PEEK, Ultem® or other similar polymer materials, such as polycarbonate, polystyrene, ABS, acrylics, polyetherimide, polyimide, polyethersulfone, polyphenylsulfone, polymethylmethacrylate, any fiber filled variation of these polymers, any amorphous polymeric material, or any other bio-compatible injection moldable polymer. In addition, as will be discussed more fully below, block 10 may include certain portions which are constructed of different and/or additional material.

As shown in FIG. 1-3, J-block 10 has a J-shape which allows for the block to be mounted, for example, on the distal portion of a femur, from several different aspects. In each aspect, block 10 is preferably capable of wrapping around at least a portion of the bone. For example, J-block 10 may be mounted medially or laterally on a distal portion of a femur with a portion of the block extending around to either the anterior or posterior portion of the bone. Clearly, several different mounting positions may be realized.

Figure 4:
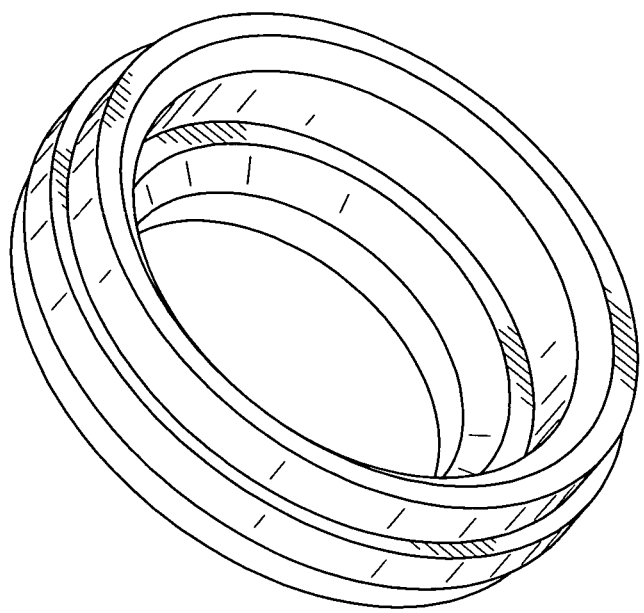
FIG. 4 is a top perspective view of a bushing for use with the J-block shown in FIGS. 1-3.

Although many different specific designs for J-block 10 may be realized, FIGS. 1-3 depict one such design. In the embodiment depicted in those figures, block 10 includes a substantially polymeric body 12 defining a bone engaging or abutting surface 14 and a cutting instrument guiding surface 16. Further, the aforementioned J-shaped block 10 also preferably includes a plurality of apertures 18 extending through body 12 adapted to receive bone pins, bone screws or the like. Such apertures may be of any size and or shape suitable for receiving such bone mounting elements. In addition, in certain embodiments, apertures 18 may be lined with a metal or other hardened material in order to ensure a solid connection with the bone surface. In fact, any portion of block 10 may be similarly lined or otherwise reinforced by another material having stronger and/or harder material property than that of the polymeric material utilized in construction of body 12. Finally, block 10 also preferably includes a central opening 20 adapted to receive a bushing or the like, such as bushing 22 depicted in FIG. 4. This opening 20 and bushing 22 are preferably designed to capture a positioning instrument such as a handle or navigation tracker. Clearly, this may allow for block 10 to be more easily manipulated and situated within the often confined space of a cavity created for performing a surgical procedure, such as a total knee arthroplasty, within. In addition, bushing 22 may help ensure that pin holes utilized in mounting block 10 do not have draft angles, which may affect how block 10 is mounted to a bone. It is noted that bushing 22 may be constructed of various materials, including certain metallic materials, such as stainless steel, cobalt chrome, titanium, etc.

Similar to the varying individual designs of block 10, many different manufacturing processes may be undertaken in order to produce such a block. For example, J-block 10, as shown in FIGS. 1-3, may be molded from polymeric material, fiber composite polymeric material or other suitable material. Such molding processes are well known in the industry and to those of ordinary skill in the art, and essentially involve infusing a mold or the like with flowable polymeric or other material and allowing such to cure. In order to save material, it is contemplated to provide block 10 with a series of cut outs or voids 24 which are preferably spaced on top or guiding surface 16 and a bottom surface 17 of the block. Providing such voids may result in less polymeric material being required in the manufacture of body 12, which in turn results in less costs associated with providing material. In addition, the lack of additional material may result in a significant reduction in overall weight of block 10. Voids 24 may be dictated by the particular mold design, should such be utilized in the manufacturing process of block 10.

Further, with regard to the manufacture of J-block 10, as mentioned above, it is contemplated to provide apertures 18, opening 20 and/or other portion of body 12 with a metal or other hardened material layer. This may be done during molding or even subsequent thereto. Clearly, such processes may increase the costs of manufacturing the block and may result in a heavier block. While certain particular manufacturing procedures for use in the production of block 10 are described above, it is clear that many different processes may be employed to produce many different block designs. For example, should the aforementioned voids 24 not be desired on the top and bottom surfaces of block 10, the particular manufacturing process may be altered. As mentioned above, in such a case, a mold being utilized may simply not include structures for ultimately producing voids 24 during the molding process. In addition, it is to be understood that those of ordinary skill in the art would readily recognize the many different manufacturing procedures which may be employed to produce a cutting block such as J-block 10.

Figure 5:
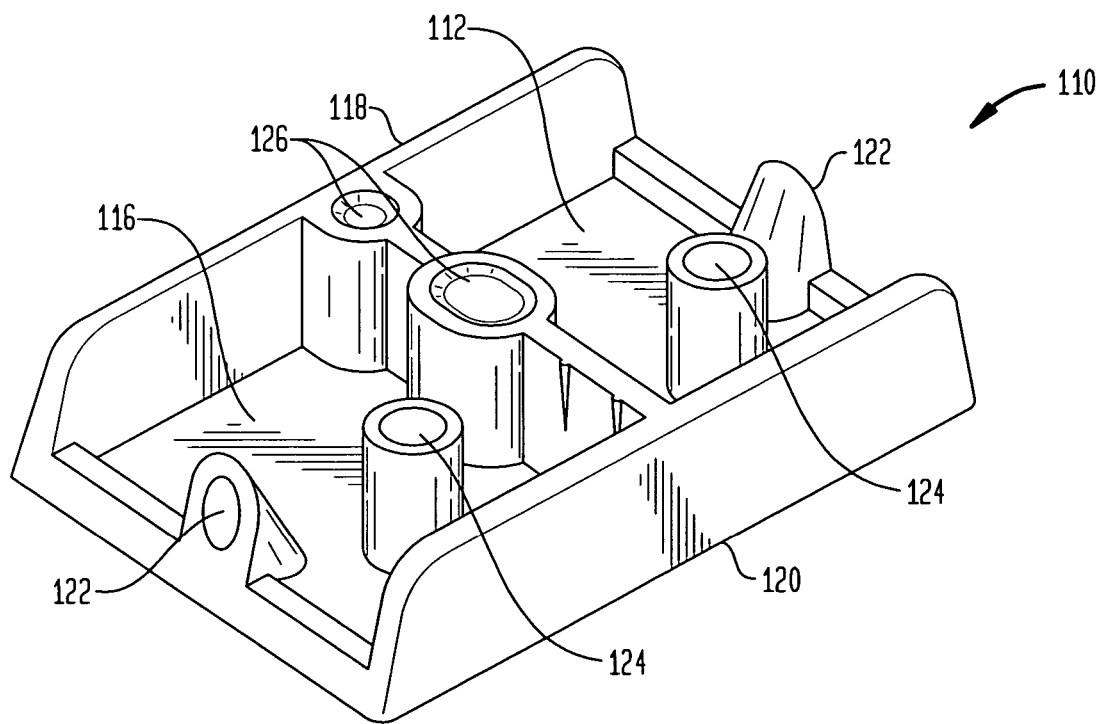
FIG. 5 is a perspective view of the distal facing surface of an anterior posterior resection block according to the present invention.
Figure 6:
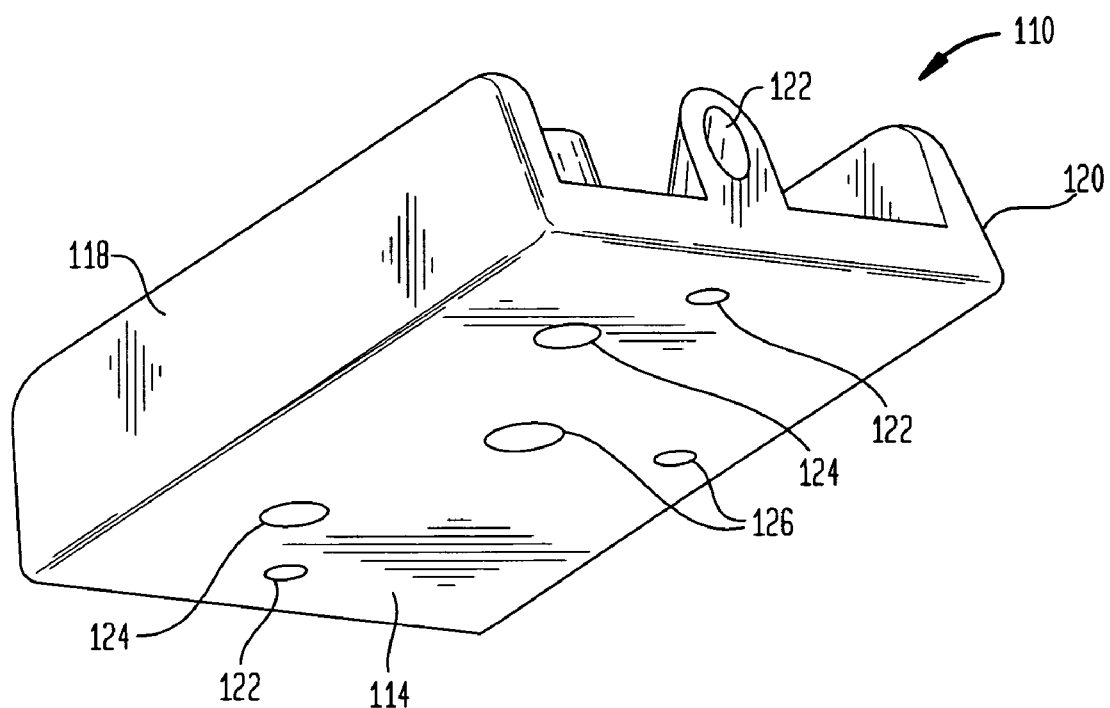
FIG. 6 is a perspective view of the bone facing surface of the anterior posterior resection block shown in FIG. 5.

In accordance with the present invention a second cutting block is depicted by itself in FIGS. 5 and 6. This cutting block is best described as a femoral anterior posterior resection guide or block and will be designated throughout with reference numeral 110. Preferably, block 110 is adapted to cooperate with a partially prepared distal end of a femur and aid in making cuts along the anterior and posterior sides of the femur. The method of utilizing block 110 will be discussed further below. Like that of block 10, anterior posterior resection block 110 is preferably constructed of polymeric material, such as those mentioned above. However, other materials may also be utilized. In the embodiment depicted in the figures, block 110 preferably includes a body portion 112 which is constructed substantially of such polymeric material or the like. Body 112 preferably defines a bone engaging surface 114, a top surface 116, an anterior cutting instrument guiding surface 118, and a posterior cutting instrument guiding surface 120. Further, body 112 includes exterior bone pin apertures 122, interior bone pin apertures 124 and supplemental guide receiving apertures 126.

Like block 10, block 110 may be of many different designs, constructed of many different types of materials, and many different manufacturing processes may be undertaken in order to produce such a block. For example, in accordance with the present invention, although shown in the figures as having a non-solid top surface 116, an embodiment of block 110 may be provided having a solid top surface. In fact, a solid cubic block, similar in functional design to block 110 is specifically contemplated. However, the non-solid top design of block 110 shown in FIGS. 5 and 6 may reduce the overall amount of material being utilized, thereby reducing the overall cost and weight of the block. In addition, like that of above-discussed block 10, the various apertures of block 110 may be provided with metal or other hardened material liners, as may other portions of block 110. This may increase the level of connectability of the block to a bone surface, while also increasing the costs and weight of block 110.

Figure 7:
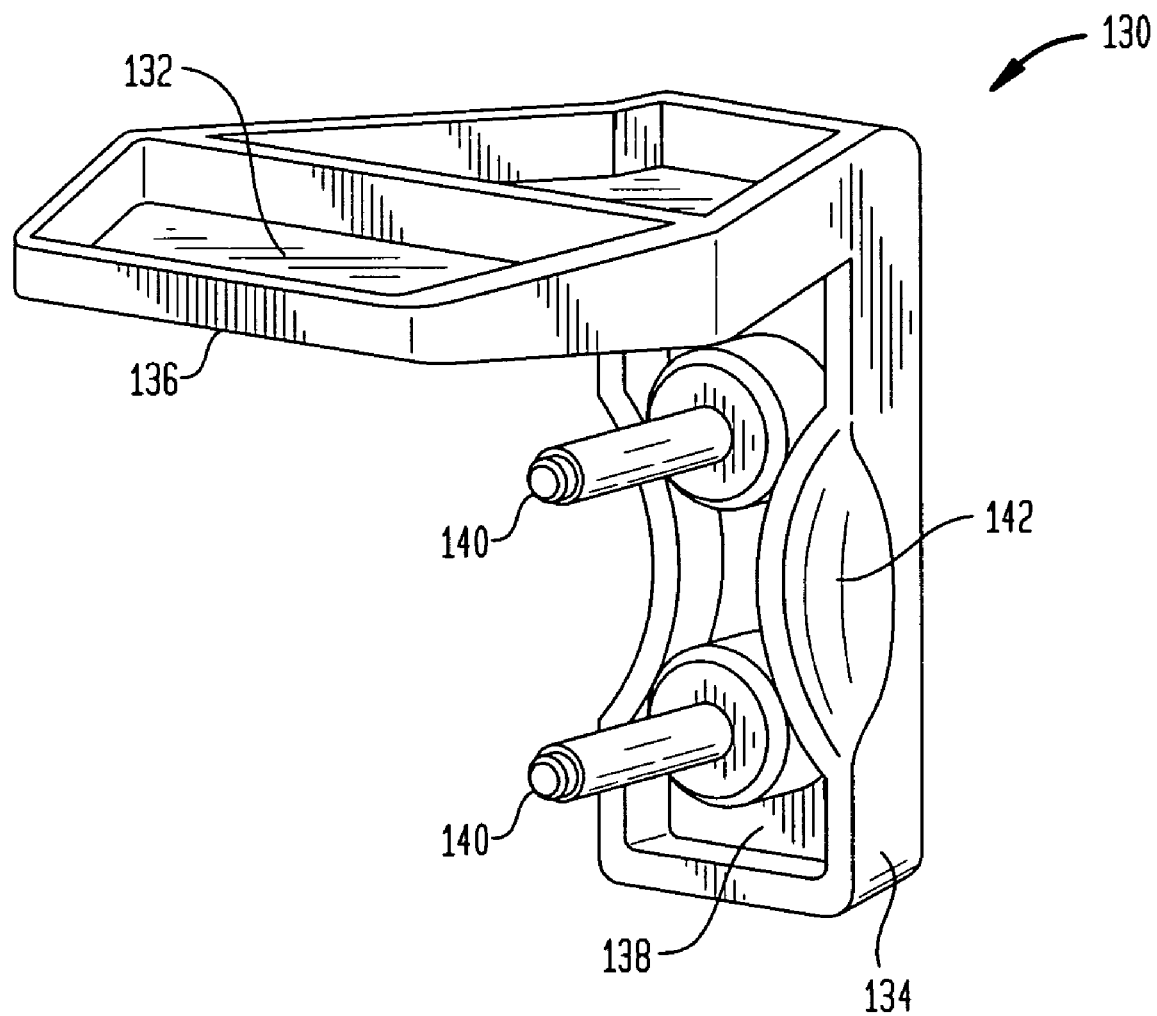
FIG. 7 is a perspective view of a femoral skim reference guide according to the present invention.
Figure 8:
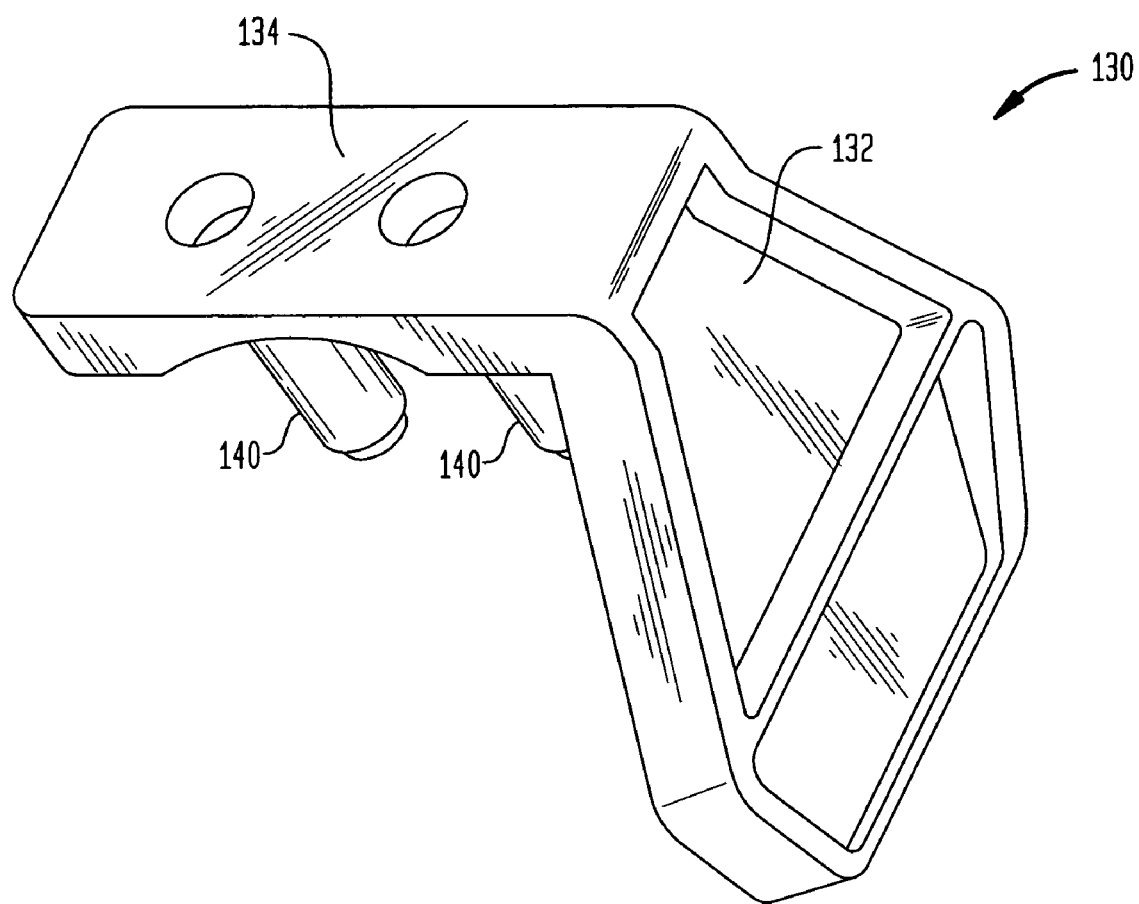
FIG. 8 is another perspective view of the femoral skim reference guide shown in FIG. 7.

FIGS. 7 and 8 depict a femoral skim reference guide 130 useful in positioning block 110 on the distal end of a partially prepared femur. Reference guide 130 is, like blocks 10 and 110, also preferably constructed of a polymeric or other suitable low cost material. In the construction depicted in the figures, guide 130 is L-shaped and preferably includes a first portion 132 and a second portion 134 positioned substantially perpendicular to first portion 132. First portion 132 further includes a substantially flat surface 136 for engaging a previously prepared skim cut or the like. This will be discussed more fully below in the discussion relating to the method of performing a surgical procedure. Second portion 134 further includes a surface 138 and extensions 140 suitable for engaging top surface 116 and supplemental guide receiving apertures 126 of block 110, respectively. In addition, guide 130 may also include depressions or access points 142 adapted to aid in the removal and/or placement of guide 130.

Figure 9:
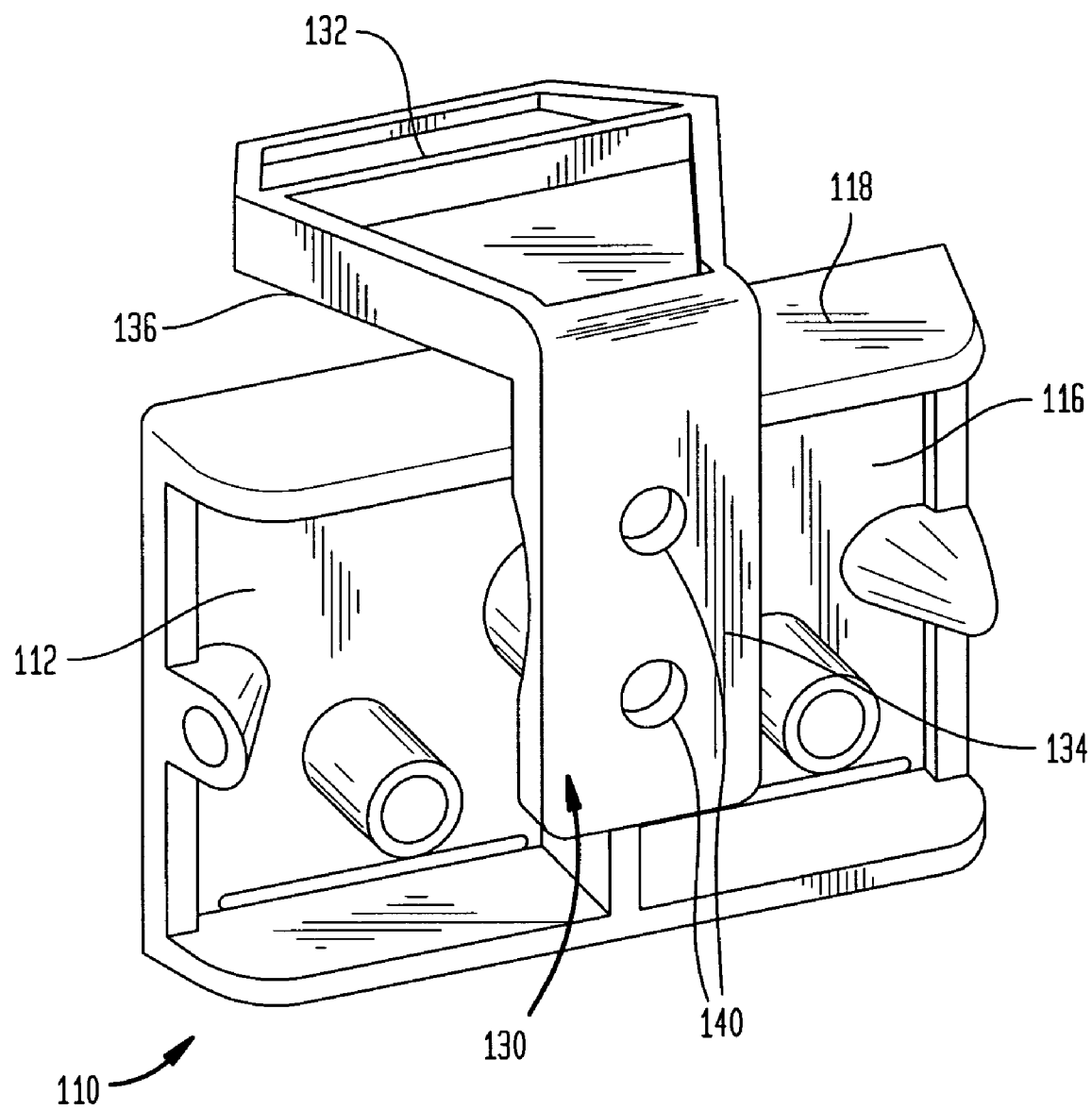
FIG. 9 depicts a distal face of the assembled anterior posterior resection block of FIGS. 5 and 6 and the femoral skim reference guide of FIGS. 7 and 8.
Figure 10:
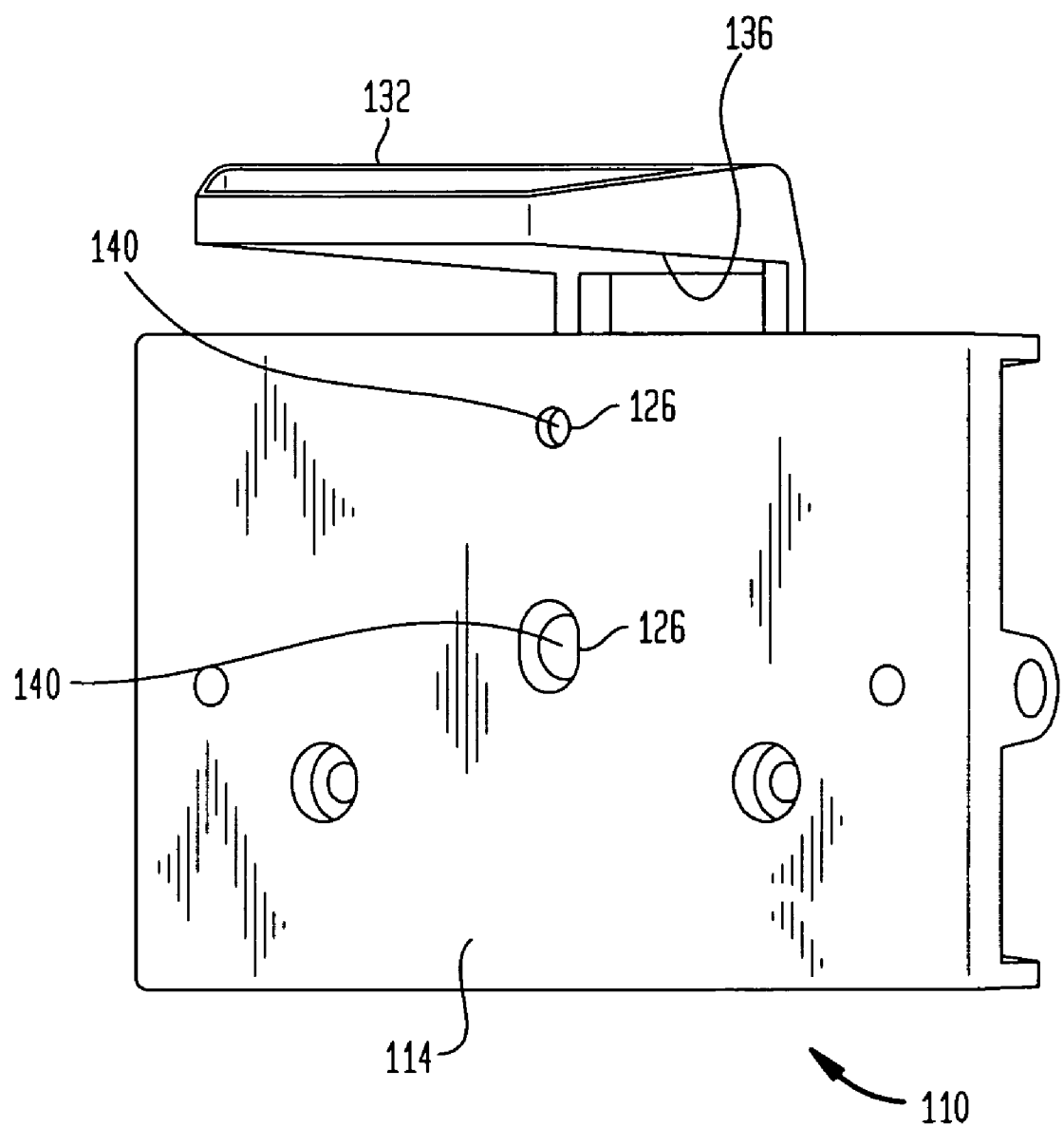
FIG. 10 depicts a proximal face of the assembly depicted in FIG. 9.

FIGS. 9 and 10 illustrate the cooperation between block 110 and its related guide 130. In assembly, guide 130 is preferably situated with respect to block 110 so that surface 138 of the guide aligns with top surface 116 of the block, and extensions 140 of the guide align with apertures 126 of the block. Thereafter, extensions 140 of guide 130 are preferably fully inserted into apertures 126 so that surface 138 abuts or lies adjacent to top surface 116. This fully assembled position is best shown in FIGS. 9 and 10. In this position, first portion 132 of guide 130 and its substantially flat surface 136 extends over anterior guiding surface 118 and past bone engaging surface 114 of block 110. This provides an extension that extends from block 110 and may be utilized to as a reference arm or extension to positively position the block with respect to certain surfaces of the distal end of a femur. This will also be more fully discussed below in the discussions relating to the use of block 110.

Figure 11:
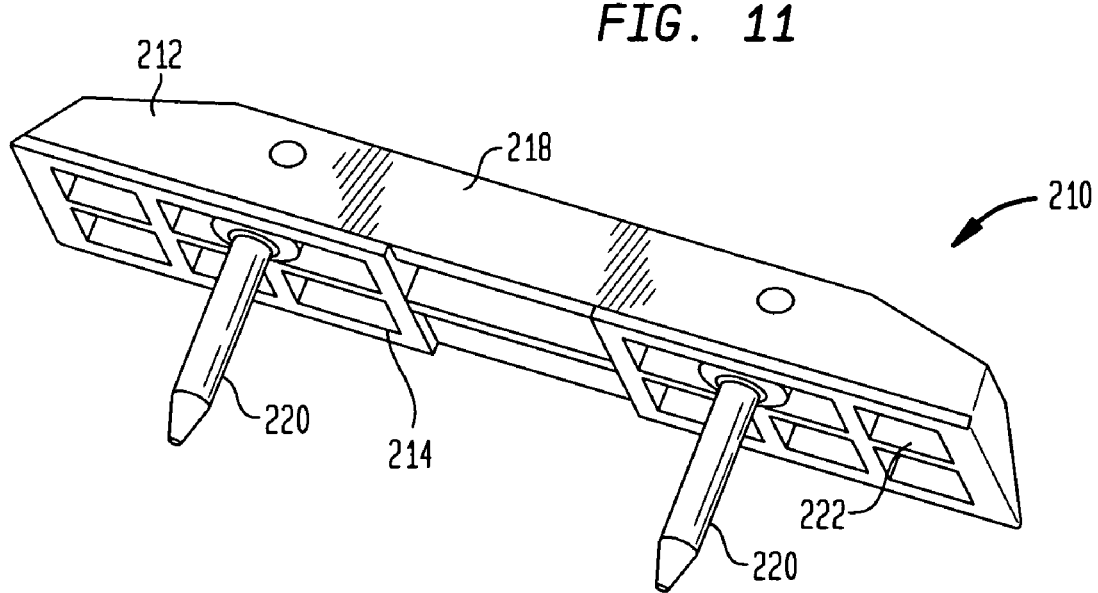
FIG. 11 is a perspective view of the proximal surface of a femoral chamfer resection block according to the present invention.
Figure 12:
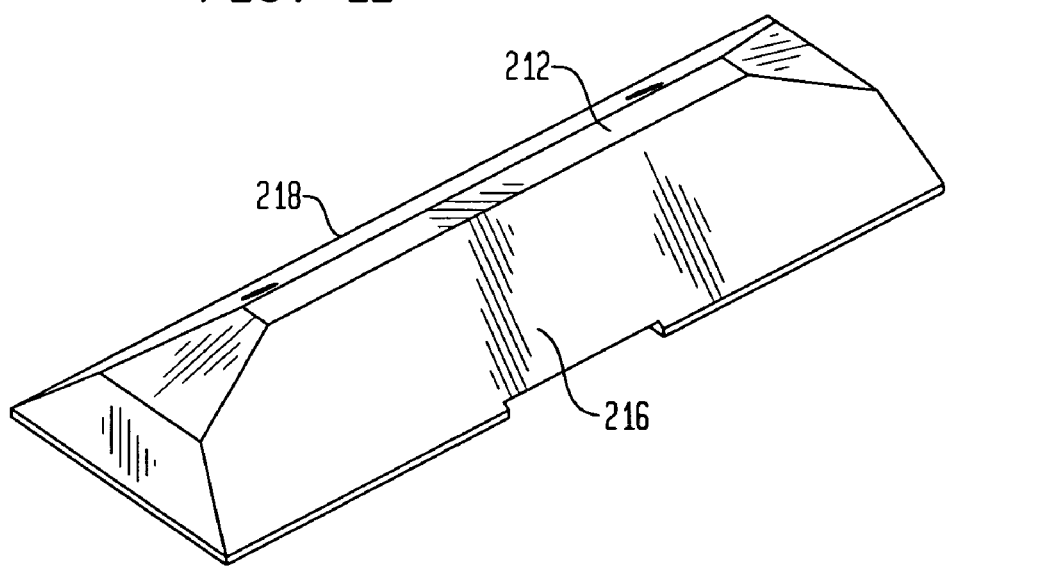
FIG. 12 is a perspective view of the distal facing surface of the femoral chamfer resection block shown in FIG. 11.
Figure 13:
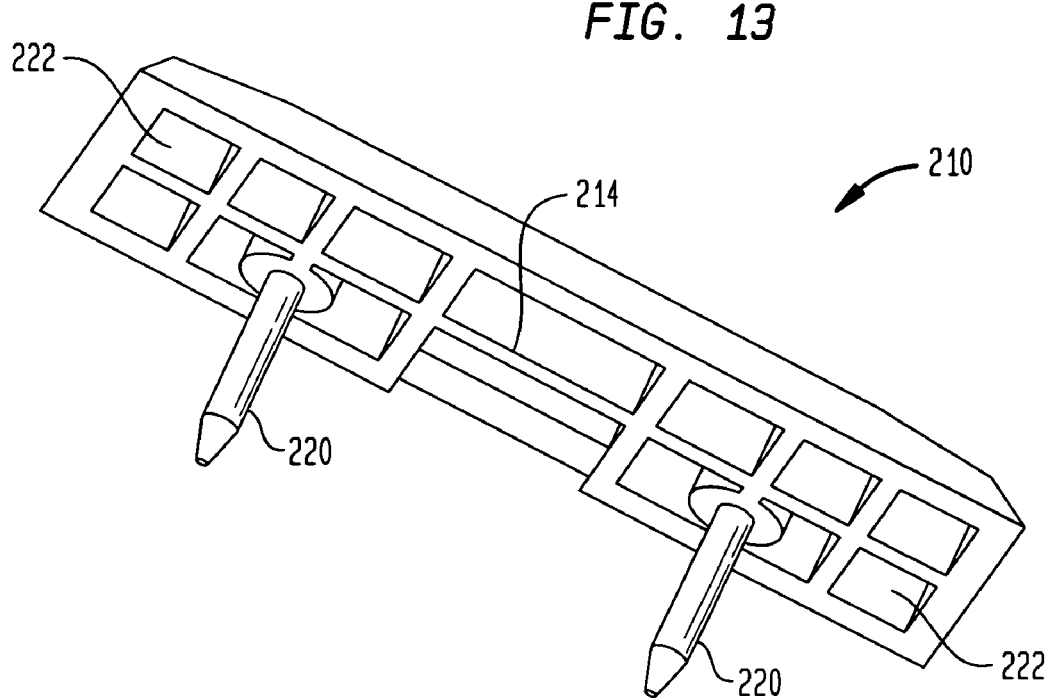
FIG. 13 is a perspective view of the bone contacting surface of the femoral chamfer resection block shown in FIG. 11.

A third cutting block according to the present invention is depicted in FIGS. 11-13. This cutting block is best described as a chamfer resection block and will be designated with reference numeral 210 throughout. Chamfer block 210 is preferably useful in aiding in making anterior and posterior chamfer cut on the distal end of a partially prepared femur. Essentially, like that of the above-described blocks 10 and 110, block 210 is a unitary body preferably constructed of a polymeric material or the like. Similarly, block 210 is capable of being manufactured or otherwise produced through like procedures. In the preferred embodiment depicted in FIGS. 11-13, chamfer resection block 210 includes a body 212 defining a bone engaging surface 214, an anterior chamfer guiding surface 216 and a posterior chamfer guiding surface 218. In addition, block 210 preferably includes one or more bone pins 220 extending from bone engaging surface 214. Such pins may be permanently affixed to block 210, or may be of a modular design. These bone pins may be any type of suitable bone engaging means, and are preferably spaced apart on surface 214 in a fashion that corresponds to the aforementioned interior bone pin apertures 124 of block 110. This correspondence is important in the method of preparing the distal end of a femur and will be more fully discussed below.

Chamfer resection block 210, like that of the above discussed blocks, may also include a plurality of cut outs or voids 222 which are created during the manufacture of the block. Once again, these voids 222 may allow for less polymeric or like material to be utilized in manufacturing the block, and thereby reduce the overall cost and weight of block 210. Finally, as shown in FIGS. 11 and 12, block 210 may include indicia or other symbols relating to the positioning and/or size of the block. For example, as shown in the figures, block 210 includes indicia identifying anterior and posterior chamfer guiding surfaces 216 and 218.

Figure 14:
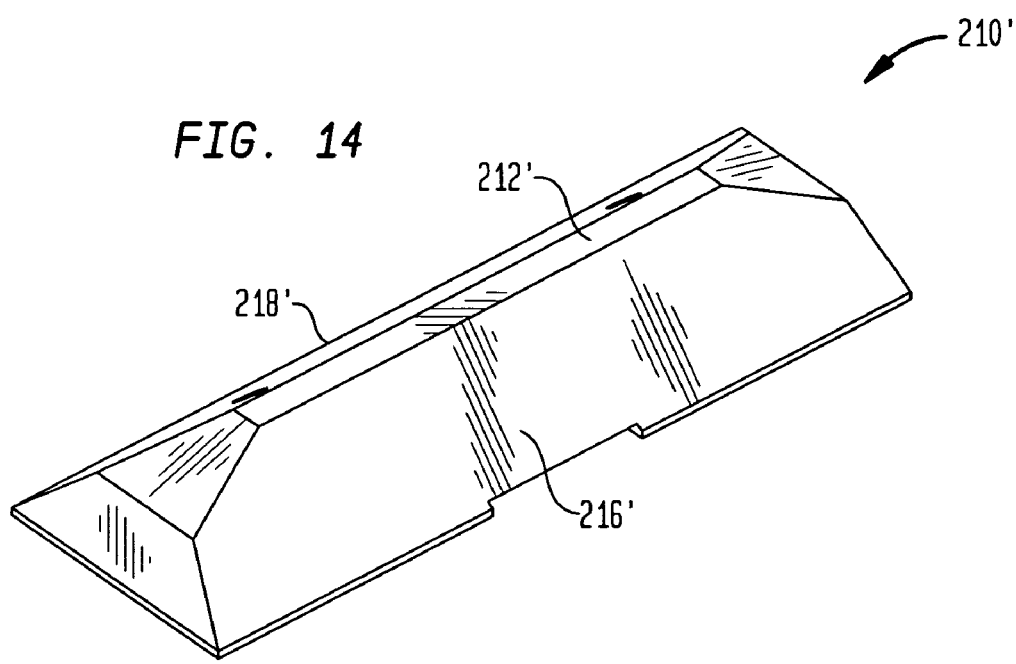
FIG. 14 is a perspective view of the distal facing surface of another embodiment femoral chamfer resection block according to the present invention.
Figure 15:
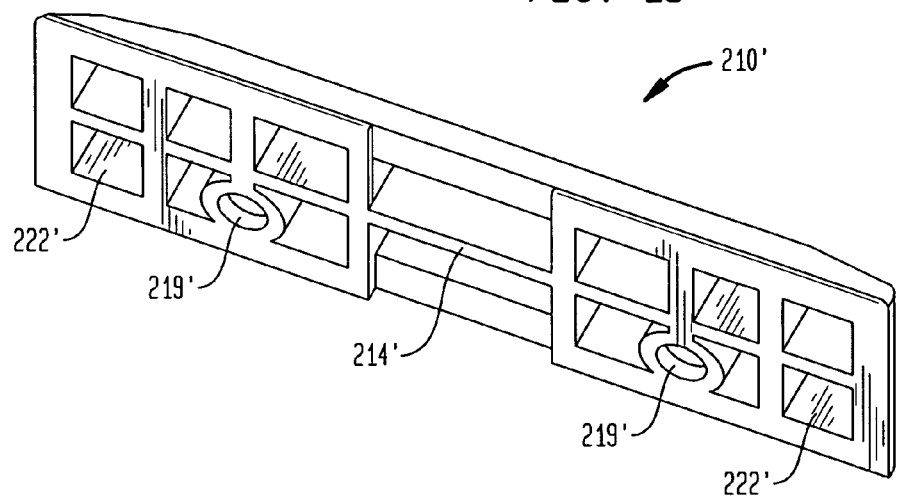
FIG. 15 is a perspective view of the bone contacting surface of the femoral chamfer resection block shown in FIG. 14.
Figure 16:
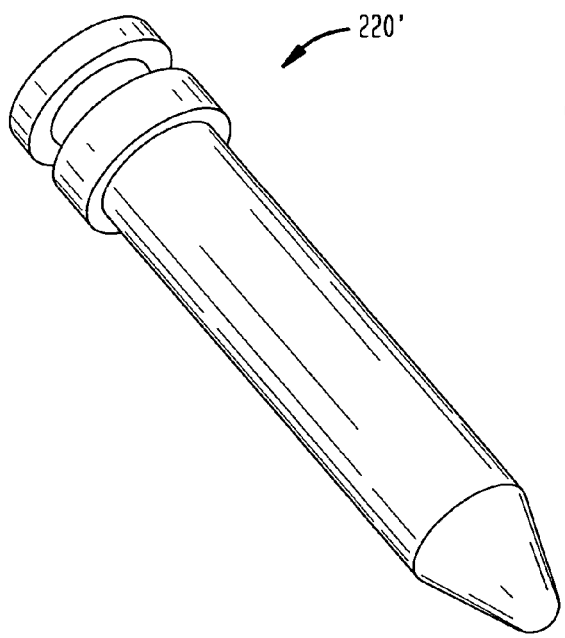
FIG. 16 is a side perspective view of a chamfer pin for use in conjunction with the femoral chamfer resection block depicted in FIGS. 14 and 15.
Figure 17:
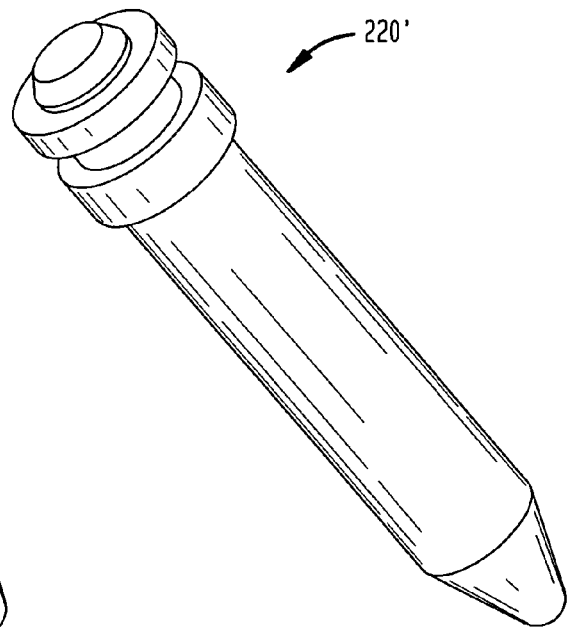
FIG. 17 is a top perspective view of the chamfer pin shown in FIG. 16.

A further embodiment of the above-discussed chamfer resection block is depicted in FIGS. 14 and 15. Essentially, this block (referred to throughout with reference numeral 210') includes similar elements to that of block 210, with each element sharing a like reference numeral with a prime indicator attached thereto. For example, block 210' includes an anterior chamfer guiding surface 216', similar to anterior chamfer guiding surface 216 of block 210. However, block 210' differs from block 210 in that it does not include built in bone pins 220. Rather, block 210' includes apertures 219' for receiving bone pins 220', such as those depicted in FIGS. 16 and 17. It is noted that the particular bone pin 220' structure may vary, as can the particular aperture 219' structure accordingly. As shown in the figures, pins 220' are designed so as to snap fit within apertures 219'. However, it is contemplated that many other designs may be employed. For example, threaded pins 220' may be provided which screw into correspondingly threaded apertures 219'. Those of ordinary skill in the art would recognize the many different configurations which may be employed.

The aforementioned different embodiment cutting blocks are all designed so as to be substantially constructed of a low cost material, such as polymers or the like. Given that such materials are often less durable and/or hard than typically utilized metals, it may be necessary to utilize special cutting tools during resections of bone material. For example, blocks 10, 110, 210 and 210' may not be suitable for use with standard well-known oscillating cutting instruments, where the entire saw blade oscillates at a high speed, as cooperation with such instruments may cause the blocks to chip or otherwise deform along their respective cutting guide surfaces. Thus, it is contemplated to utilize cutting tools, such as saw blades that do not operate in such a fashion. Specifically, in certain embodiments, it is contemplated to utilize cutting tools which employ more static elements being supported by the cutting block surfaces in conjunction with blocks 10, 110, 210 and 210'.

Figure 18:
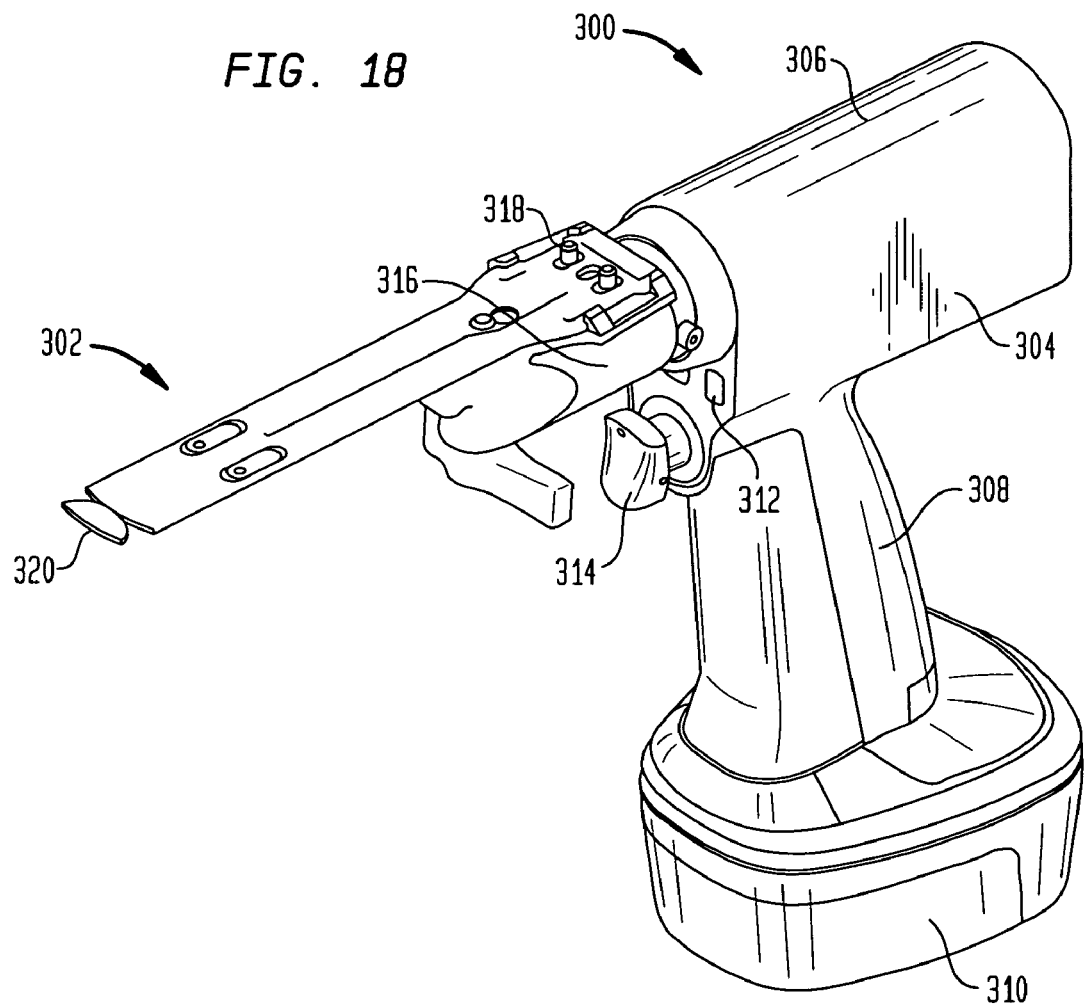
FIG. 18 is a perspective view of a surgical sagittal saw with a saw blade head attached for use in accordance with the present invention.

One example of such a cutting instrument is broadly depicted in FIG. 18 and referred to throughout with reference numeral 300. Although briefly described below, surgical saw 300 is the subject of and more particularly described in U.S. patent application Ser. No. 10/887,642, filed on Jul. 9, 2004 and U.S. Patent Application No. 60/715,821, Sep. 10, 2005 (collectively referred to as "the surgical saw patents"). Both of the disclosures of the surgical saw patents are hereby incorporated by reference herein. Essentially, as is more fully set forth in the surgical saw patents, saw 300 includes a blade assembly 302 and a housing 304. Housing 304 preferably includes an elongated, top-located barrel section 306, a pistol-grip shaped handle 308, a motor (not shown) disposed within barrel section 306, and a battery 310 removably attached to the butt end of handle 308. A front plate 312 is also fitted over the distal end opening of barrel section 306, and a trigger 314 is moveably mounted to the front plate. A control circuit (not shown) is preferably housed within handle 308 for monitoring actuation of trigger 314. Based upon the extent to which trigger 314 is actuated, this control circuit selectively energizes the motor to cause such to rotate at a desired speed.

Further, a saw head 316 extends forward from front plate 312 above trigger 314. The proximal end of blade assembly 302 is preferably removably fitted to head 316. Internal to head 316 is an oscillating head (not shown) which includes a pair of pins 318. Essentially, when blade assembly 302 is mounted to saw head 316, drive rods (not shown) engage pins 318. When the motor is actuated, the oscillating head and pins 318 oscillate, thereby causing the drive rods to reciprocate. Finally, a blade head 320 forms the most distal end of the blade assembly 302, with the aforementioned drive rods being attached thereto. The reciprocal movement of the drive rods causes blade head 320 to therefore oscillate back and forth in a cutting motion. In all, this means that the only exterior portion of blade assembly 302 which moves resides at its distal tip, i.e.—blade head 320. In addition, it is noted that blade head 320 is preferably situated at a different level than the remainder of assembly 302. Thus, as long as only the non-moving remaining portions of blade assembly 302 contact the respective polymeric guide surfaces of the above-described polymeric cutting blocks, even during initial cutting operations. Clearly, the aforementioned problems with such blocks becoming damaged or deformed may be avoided and provides a situation which is extremely beneficial to the orthopedic industry, as these relatively cheap and previously unusable cutting blocks, may now be utilized without fear of such drawbacks.

Obviously, the above description of saw 300 is a description of only one suitable device. In fact, the surgical saw patents include several embodiments which may be suitable for use with blocks 10, 110, 210 and 210'. In addition, it is to be understood that these blocks are not limited to use with this particular type of cutting instrument. Depending upon the material utilized in constructing the blocks, such may be used with well-know cutting instruments. For example, sufficiently hard polymers may be used in conjunction with normal oscillating saws. Additionally, other cutting instruments may exist that can be useful for use with blocks 10, 110, 210 and 210'. Those of ordinary skill in the art would readily recognize suitable cutting instruments.

One surgical method will now be described which make use of the above-described blocks and cutting instruments. Although this method relates to the use of such blocks during a total knee arthroplasty, it is to be recognized that each block may have utility in other surgical methods. For example, one or more of blocks 10, 110, 210 and/or 210' may be utilized in a partial knee arthroplasty. In addition, certain of the blocks may be utilized in surgeries involving other portions of the body of a patient. Similarly, those of ordinary skill in the art would recognize that minor modifications in the size and/or shape of the above-described blocks and the below method may allow for operating on different body portions and/or or differently sized patients. Finally, although one particular surgical method is set forth below, it is to be understood that different and/or additional steps may be performed to achieve the same goal. For example, while discussed as being a total knee arthroplasty without attention to incision size or the like, blocks 10, 110, 210 and 210' may be utilized in minimally invasive procedures or the like.

Figure 19:
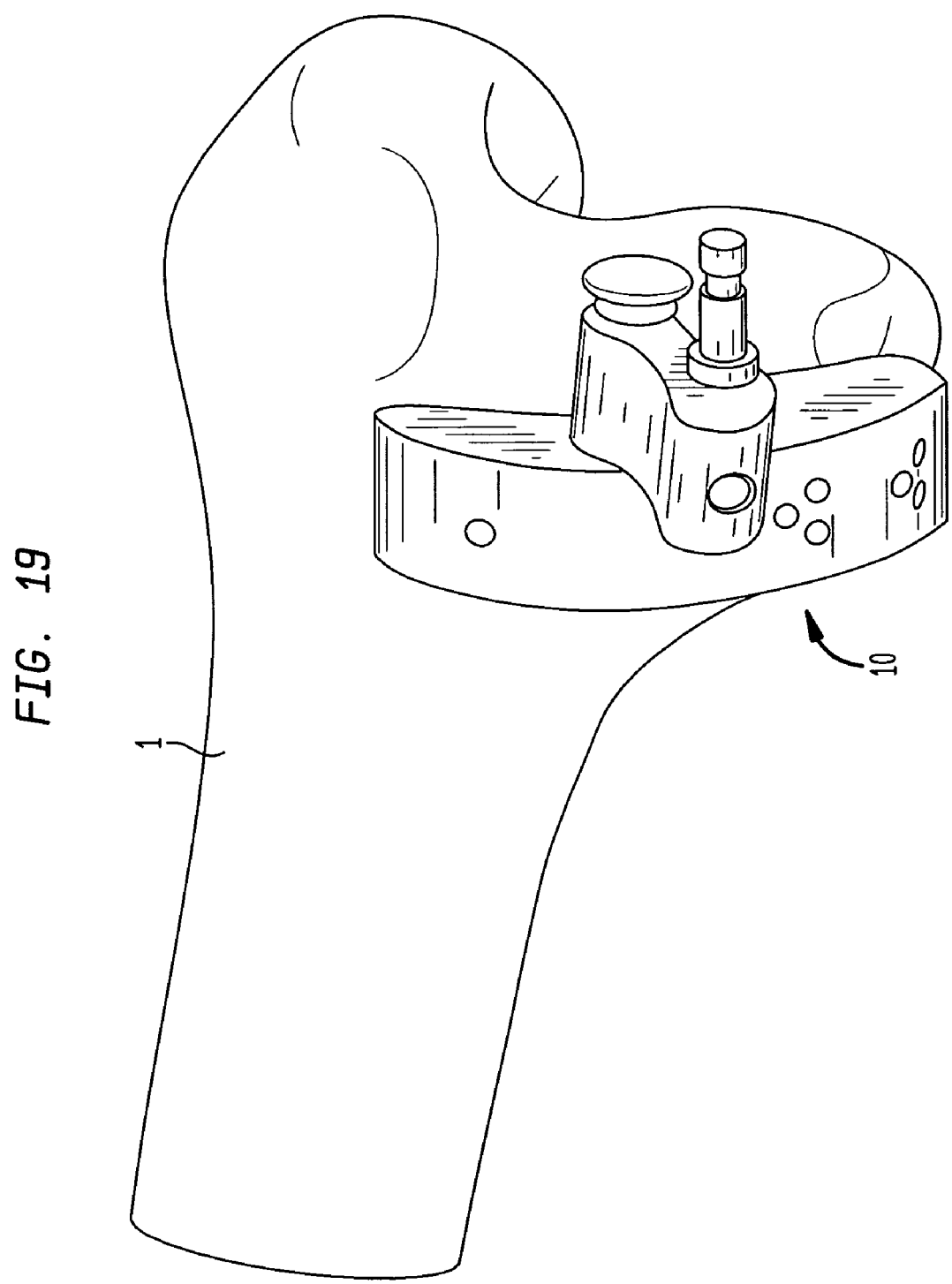
FIG. 19 illustrates the J-block of FIGS. 1-3 mounted to a distal portion of a femur with a navigation tracker attached thereto.

Initially in the surgical method, a surgeon will make an incision in the knee portion of a patient in order to expose both the distal end of the femur and the proximal end of the tibia. The femur will be designated with reference numeral 1 for the below discussions, and the tibia and tibial preparation steps will not be discussed herein. The latter being readily apparent to those of ordinary skill in the art. With the distal end of femur 1 being exposed, a surgeon first mounts J-block 10 on any one of the sides of the femur (best shown in FIG. 19). As discussed more fully above, J-block provides a design suitable for mounting on many different sides of the femur in order to provide many different cutting aspects to the surgeon. In the example depicted in FIG. 19, block 10 is positioned on the medial side of the left femur 1 of a patient. In order to mount the block to the bone material, well known bone pins or screws may be utilized in conjunction with apertures 18. In addition, it is noted that J-block 10 may be positioned and mounted by utilizing many different types of the guiding devices, such as intramedullary and extramedullary rods, and navigations apparatus. Such are well known in the art and may easily be adapted to cooperate with a block such as block 10, or the other blocks described herein.

Figure 20:
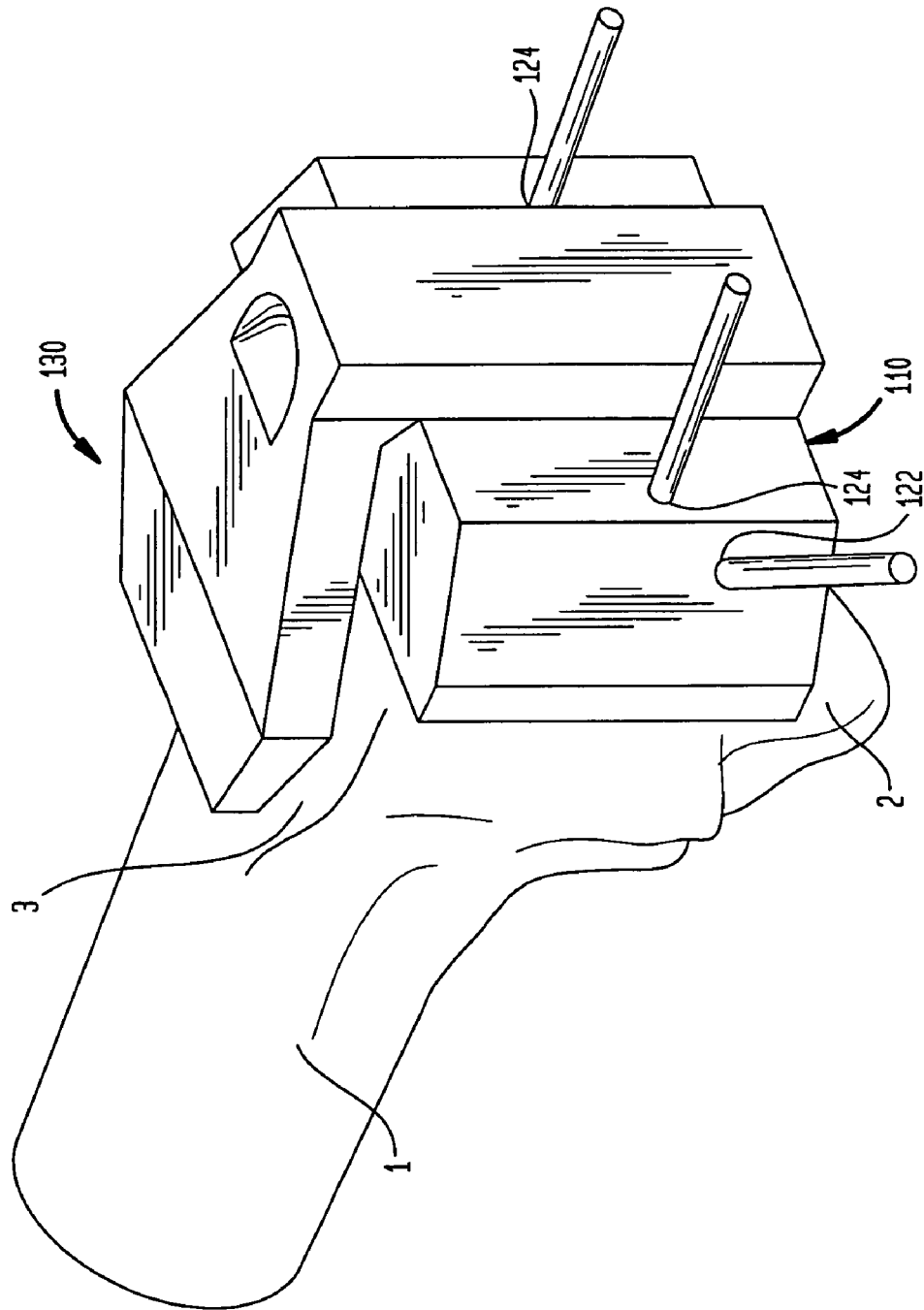
FIG. 20 illustrates the anterior posterior resection block of FIGS. 5 and 6 and the femoral skim reference guide of FIGS. 7 and 8 mounted to a distal portion of a partially resected femur.

With block 10 properly mounted, a surgeon preferably utilizes a surgical saw, like saw 300, in conjunction with either surface 16 or surface 17. Essentially, the surgeon rides blade assembly 302 of saw 300 along either of these surfaces while blade head 320 cuts or resects the distal end of femur 1. It is the goal during this step of the method to provide one single flat surface extending across the distal end of femur 1. This single flat surface is important in the subsequent steps of this method, and is best shown in FIG. 20 as surface 2. Once this flat surface is created, J-block 10 and any pins or other means utilized to mount the block to the bone may be removed. The relatively inexpensive nature of block 10 allows such to be disposed of upon completion of the cut. Alternatively, block 10, and any other blocks or instruments utilized may be disposed of upon completion of the entire surgical procedure.

Subsequent to removing J-block 10, the surgeon preferably creates a skim cut, which is shown in FIG. 20 and labeled with reference numeral 3. This skim cut 3 may be created by utilizing saw 300 or the like, and may or may not be created through the use of an additional guide or block. As shown in FIG. 20, cut 3 essentially acts as a reference surface for flat surface 136 of guide 130 to abut. Given the assembled cooperation between block 110 and guide 130, placement of flat surface 136 on cut 3 preferably aligns block 110 into place on surface 2. Once block 110 is aligned on surface 2, pins or the like may be inserted through pin apertures 122 and into the bone material of femur 1, and guide 130 may be removed and disposed of. This leaves block 110 mounted to the partially prepared distal end of femur 1.

With block 110 in position, saw 300 or the like may be utilized to complete cuts on both the anterior and posterior sides of femur 1. Essentially, the surgeon guides saw 300 or another suitable cutting instrument along anterior and posterior guiding surfaces 118 and 120, in order to create the relatively straight anterior and posterior resections best shown in FIG. 21 and labeled as surfaces 4 and 5 respectively. In addition, either prior to or subsequent to making the cuts which create surfaces 4 and 5, pins or the like may be inserted through interior bone pin apertures 124 and into the bone material of femur 1. It is noted that such pins may be sized so as to remain in place during removal of block 110, or so as to further hold the block in place. Whatever the case, subsequent to making the cuts that form surfaces 4 and 5, block 110 is preferably removed and disposed of. Should the pins inserted through apertures 124 remain in place, such would remain extending from surface 2 of femur 1. Alternatively, should such pins be removed, two spaced apart holes preferably remain in the surface.

With surfaces 2, 4 and 5 having been made, the surgeon now preferably positions chamfer resection block 210 or 210' on surface 2. If the aforementioned pins inserted through apertures 124 of block 110 remain, block 210' may be connected thereto through the cooperation between the pins and apertures 219'. Alternatively, should only holes remain in surface 2, bone pins 220 of block 210 may be inserted therein. In this regard, it is noted that bone pins 220 of block 210 would preferably have a larger diameter than that of the aforementioned holes created by pins inserted through apertures 124 of block 110. Whatever the case, it is noted that interior bone pin apertures 124 of block 110 are preferably spaced apart the same distance as that of either apertures 219' of block 210' or bone pins 220 of block 210. Thus, the use of block 110 not only aids in the making of cuts which create surfaces 4 and 5, but also in further positioning either block 210 or 210'.

Figure 21:
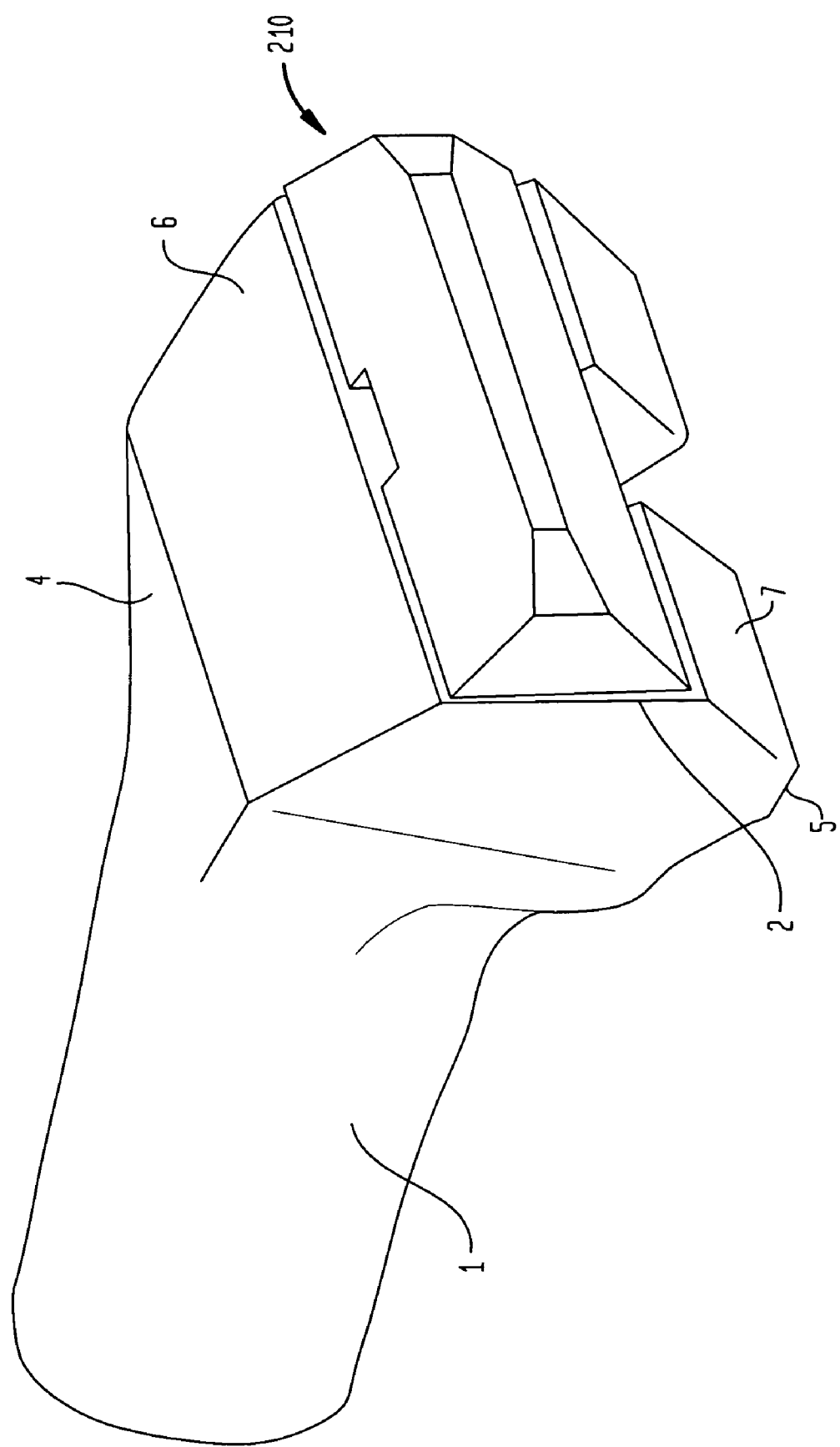
FIG. 21 illustrates any of the femoral chamfer resection blocks of FIGS. 11-15 mounted to a distal portion of a partially resected femur.

Once properly positioned and connected to the distal end of femur 1, block 210 or 210' is preferably utilized to make necessary chamfer cuts. More particularly, anterior and posterior chamfer guiding surfaces 216 and 218 or 216' and 218' are utilized to guide saw 300 or the like in order to make cuts that create surfaces 6 and 7, as are best shown in FIG. 21. It is worth noting that all of the aforementioned surfaces created through the use of the various blocks are necessary in mounting an implant or trial implant, which includes an interior surface that essentially conforms to surfaces 2, 4, 5, 6 and 7. This type of 5-surface cooperation is well-known in the art and would be readily apparent to those of ordinary skill in the art. Once each of the surfaces are created, block 210 or 210' may be removed and disposed of. In addition, any remaining bone pins or the like are also preferably removed from the distal end of femur 1. At this point, either an implant or trial implant may be mounted on the distal end of femur 1, and the surgeon may perform other preparatory steps for completing the total knee arthroplasty. For example, subsequent to preparing the distal end of femur 1, the surgeon may similarly prepare the proximal end of the tibia and/or prepare the patella for a patella implant. Depending upon the particular surgical technique being employed, certain of these additional steps may vary, with the ultimate goal being restoring the articulating surfaces of the knee joint.

Given the many varying types of surgery which may be performed utilizing the blocks described herein, clearly such blocks and their use may also widely vary. For example, those of ordinary skill in the art would readily recognize that such blocks may be sized and configured in order to be useful in perform resections on other bones of the body of a patient. Clearly, certain of the blocks in their form shown herein, may already be suitable for such tasks. For instance, block 10 may be useful in preparing the proximal end of the tibia of a patient during a total knee arthroplasty or the like. Similarly, the above-described blocks may be designed so as to include additional and/or different elements. For example, rather than the various cutting instrument guiding surfaces, one or more of blocks 10, 110, 210 and/or 210' may be configured so as to include a slot or other aperture suitable for guiding a cutting instrument. In such cases, the closed in guiding surfaces may ensure that a cutting blade or the like does not move away from the guiding surface, thereby lowering the overall accuracy and precision of the cut surface created in the bone material being prepared.

In addition, it is to be understood that blocks 10, 110, 210 and 210' may also be varied in size in order to aid in the surgery of differently sized patients. For example, several differently sized variations of blocks 10, 110, 210 and 210' may be provided in single or multiple kits for use during a surgical procedure. In addition to coupling differently sized blocks together, such blocks may also be coupled with cutting blades (such as cutting assembly 302 of saw 300) in a kit. This may provide the surgeon with one single kit useful in completely an entire surgery on many differently sized patients. In addition to such convenience, the single package or kit may also lower the costs associated with sterilizing all of the instruments and/or blocks, as all of the elements may be sterilized in one sterilization procedure. Similarly, each of these components may be contained within a single sterilized package.

Clearly, the aim of the present invention is to provide one or more blocks constructed of a low cost material that can be aligned with or without Navigation instruments to guide a saw blade or the like to make straight resections. Essentially, the main construct of each of the blocks is made from a low cost material, such as polymer materials which can be molded. Low cost metals or other materials can also be used in conjunction with the main construct for higher loaded areas, such as pins or precision components like mating features.

Preferably, the blocks of the present invention are to be utilized to guide a low friction cutting instrument, such as the aforementioned saw 300. In addition, it is noted that the blocks in accordance with the present invention would preferably be packaged in clean and sterile packages, using a method such as Gamma Radiation to sterilize same. In fact, it is contemplated to provide blocks of a construction which would deform in an unusable or noticeable fashion should steam be utilized to sterilize same. This may reduce the chance of reuse by unknowing or careless surgeons or other medical professionals.

The single use or disposable cutting blocks of the present invention have several advantages over reusable instruments. For one, such blocks may provide an increased cutting accuracy. A reusable resection guide typically gets damaged and worn with usage, while a single use block would be accurate for its one time use. In addition, the blocks of the present invention are clean sterile instruments that would be ready and available at each case. Reusable instruments are sometimes not cleaned properly and would have to be reprocessed, which could delay surgery if a second instrument is not readily available. In addition, instruments wit holes or cavities are difficult to clean. Thus, their initial sterilized natured make the blocks of the present invention useful in reducing the chance of infection in a patient. Clearly, an unsterile instrument has a higher chance of going undetected in a reusable instrument than in a single use instrument. Not having to sterilize the instruments also reduces hospital processing time. Finally, the cutting blocks of the present invention may aid in improving visibility. Given that such blocks may be constructed of polymer material, it is noted that such material may be clear material. In this case, visibility may be increase for alignment, pinning and even cutting/resection.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of performing a surgical procedure on a patient comprising:
   providing at least one cutting block constructed of polymeric material, the cutting block having at least one guiding surface;
   providing a low friction cutting instrument suitable for cutting a bone of the patient, the cutting instrument having an oscillating portion and a non-oscillating portion;
   positioning the cutting block with respect to the bone of the patient; and
   cutting a portion of the bone of the patient by guiding the low friction cutting instrument along the guiding surface of the cutting block, the cutting instrument not being interconnected with the cutting block,
   wherein the oscillating portion of the cutting instrument that cuts the bone of the patient is spaced from the guiding surface of the cutting block and the non-oscillating portion of the cutting instrument is guided by the guiding surface of the cutting block.

2. The method of performing a surgical procedure according to claim 1, wherein the surgical procedure is a total knee arthroplasty.

3. The method of performing a surgical procedure according to claim 2, wherein three cutting blocks are provided.

4. The method of performing a surgical procedure according to claim 3, wherein a first cutting block is adapted to make a single resection across the distal end of a femur of the patient, a second cutting block is adapted to make anterior and posterior resections of the femur of the patient and a third cutting block is adapted to make anterior and posterior chamfer resections of the femur of the patient.

5. The method of performing a surgical procedure according to claim 4, wherein the first cutting block is J-shaped.

6. The method of performing a surgical procedure according to claim 1, further comprising the step of affixing the cutting block to the bone of the patient.

7. The method of performing a surgical procedure according to claim 1, wherein the cutting block includes non-polymer elements.

8. The method of performing a surgical procedure according to claim 1, wherein the cutting instrument is a surgical saw including a blade assembly having an oscillating blade head.

9. The method of performing a surgical procedure according to claim 8, wherein the surgical saw further includes a motor, a battery and a trigger.

10. The method of performing a surgical procedure according to claim 8, wherein the cutting block is constructed substantially of polymeric material.

11. The method of performing a surgical procedure according to claim 1, wherein the positioning step includes the use of a navigation tracker.

12. The method of performing a surgical procedure according to claim 1, wherein the at least one cutting block is constructed of polymer selected from the group consisting of PEEK, polycarbonate, polystyrene, ABS, acrylics, polyetherimide, polyimide, polyethersulfone, polyphenylsulfone, polymethylmethacrylate and any fiber filled variation of these polymers.

13. A method of performing a surgical procedure on a patient comprising:
  providing at least one cutting block constructed substantially of polymeric material, the cutting block having at least one guiding surface;
  providing a low friction cutting instrument suitable for cutting a bone of the patient, the cutting instrument having an oscillating portion and a non-oscillating portion;
  positioning the cutting block with respect to the bone of the patient; and
  cutting a portion of the bone of the patient by guiding the low friction cutting instrument along the guiding surface of the cutting block, the cutting instrument not being interconnected with the cutting block,
  wherein the oscillating portion of the cutting instrument that cuts the bone of the patient is spaced from the guiding surface of the cutting block and the non-oscillating portion of the cutting instrument is guided by the guiding surface of the cutting block.

14. The method of performing a surgical procedure according to claim 13, wherein the surgical procedure is a total knee arthroplasty.

15. The method of performing a surgical procedure according to claim 14, wherein three cutting blocks are provided, each of the three cutting blocks being constructed substantially of polymeric material.

16. The method of performing a surgical procedure according to claim 15, wherein a first cutting block is adapted to make a single resection across the distal end of a femur of the patient, a second cutting block is adapted to make anterior and posterior resections of the femur of the patient and a third cutting block is adapted to make anterior and posterior chamfer resections of the femur of the patient.

17. The method of performing a surgical procedure according to claim 13, wherein the cutting instrument is a surgical saw including a blade assembly having an oscillating blade head.

18. The method of performing a surgical procedure according to claim 17, wherein the surgical saw further includes a motor, a battery and a trigger.

19. The method of performing a surgical procedure according to claim 13, wherein the at least one cutting block is constructed of polymer selected from the group consisting of PEEK, polycarbonate, polystyrene, ABS. acrylics, polyetherimide, polyimide, polyethersulfone, polyphenylsulfone, polymethylmethacrylate and any fiber filled variation of these polymers.

20. A method of performing a surgical procedure on a patient comprising:
  providing at least one cutting block constructed substantially of polymeric material; the cutting block having at least one guiding surface;
  providing a cutting instrument suitable for cutting a bone of the patient, the cutting instrument including a blade assembly having an oscillating blade head and a non-oscillating portion;
  positioning the cutting block with respect to the bone of the patient; and
  cutting a portion of the bone of the patient by guiding the non-oscillating portion of the blade assembly along the guiding surface of the cutting block while the oscillating blade head cuts the bone, the cutting instrument not being interconnected with the cutting block.

21. The method of performing a surgical procedure according to claim 20, wherein three cutting blocks are provided, each of the three cutting blocks being constructed substantially of polymeric material.

22. The method of performing a surgical procedure according to claim 21, wherein a first cutting block is adapted to make a single resection across the distal end of a femur of the patient, a second cutting block is adapted to make anterior and posterior resections of the femur of the patient and a third cutting block is adapted to make anterior and posterior chamfer resections of the femur of the patient.

* * * * *